United States Patent [19]
Murakami et al.

[11] 3,935,198
[45] Jan. 27, 1976

[54] PROCESS FOR THE PREPARATION OF THE CEPHALOSPORANIC ACID DERIVATIVE

[75] Inventors: Masuo Murakami; Kozo Takahashi, both of Tokyo; Ichiro Isaka, Hoya; Teruaki Ozasa, Ageo; Teruya Kashiwagi, Urawa, all of Japan

[73] Assignee: Yamanouchi Pharmaceutical Co., Ltd., Tokyo, Japan

[22] Filed: Dec. 19, 1973

[21] Appl. No.: 426,108

[30] Foreign Application Priority Data
Dec. 28, 1972 Japan.................................. 48-2755

[52] U.S. Cl............................................ 260/243 C
[51] Int. Cl.².................................... C07D 501/10
[58] Field of Search.............................. 260/243 C

[56] References Cited
UNITED STATES PATENTS
3,780,028  12/1973  Naito et al...................... 260/243 C OTHER PUBLICATIONS
Spry, J. Am. Chem. Soc. 92(16), pp. 5006–5008 (8/12/70).

*Primary Examiner*—Donald G. Daus
*Assistant Examiner*—Diana G. Rivers
*Attorney, Agent, or Firm*—Burgess, Ryan and Wayne

[57] ABSTRACT
A process for the preparation of cephalosporanic acid derivatives represented by the formula

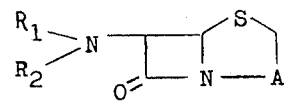

wherein $R_1$ and $R_2$, which may be the same or different, each represents a univalent group other than a hydrogen atom, said $R_1$ and $R_2$ may be combined to form a divalent group and A represents a divalent group represented by the formulae

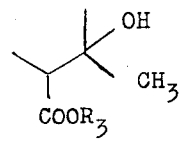 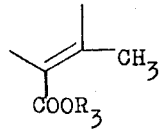

wherein $R_3$ represents a hydrogen atom or a group which does not contribute to the reaction, which comprises heating a penicillin sulfoxide derivative represented by the formula

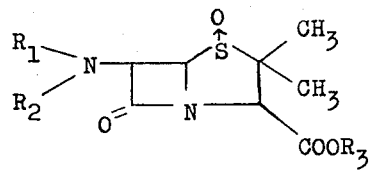

wherein $R_1$, $R_2$ and $R_3$ are as defined above.

The cephalosporanic acid derivatives prepared by the process of this invention are useful as a starting material for the preparation of antibacterials.

7 Claims, No Drawings

PROCESS FOR THE PREPARATION OF THE CEPHALOSPORANIC ACID DERIVATIVE

DETAILED DESCRIPTION OF THE INVENTION

The present invention relates to a process for the preparation of cephalosporanic acid derivative represented by the formula (II)

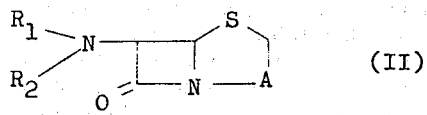

(II)

wherein $R_1$ and $R_2$, which may be the same or different, each represents a univalent group other than a hydrogen atom, said $R_1$ and $R_2$ may be combined to form a divalent group and A represents a divalent group represented by the formulae

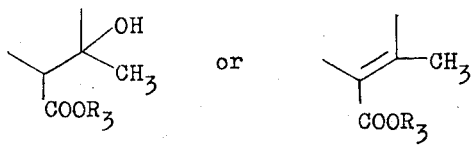

wherein $R_3$ represents a hydrogen atom or a group which does not contribute to the reaction, which comprises heating the penicillin sulfoxide derivatives represented by the formula (I)

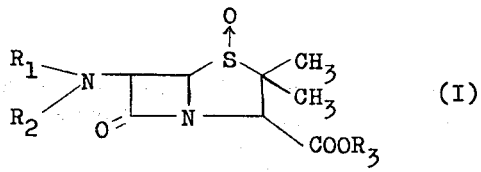

(I)

wherein $R_1$, $R_2$ and $R_3$ are as defined above.

The cephalosporanic acid derivative of the formula (II) prepared by the process of this invention are useful as a starting material for the preparation of antibacterials and also are antibacterials.

There have, hitherto, been known many processes for the preparation of cephalosporin derivatives by enlarging the rings of penicillin sulfoxide derivatives as disclosed in, e.g., the specifications of U.S. Pat. No. 3,275,626; Dutch Pat. Nos. 6,806,533 and 6,806,532; and Belgian Pat. Nos. 745,845; 747,382; 747,118; 747,119, and 747,120.

However, each of the known processes requires the use of acid catalyst. Furthermore, it has hitherto been believed that the enlargement of the ring of a penicillin sulfoxide derivative in the absence of acid catalyst is impossible.

As the results of further various investigations under such technical levels as mentioned above, the inventors have discovered that the ring of a penicillin sulfoxide derivative can be enlarged with a high yield without using an acid catalyst. That is, the inventors have discovered that when the penicillin sulfoxide derivative wherein two hydrogen atoms of the amino group at the 6-position have been substituted by other groups as shown in formula (I), the ring of the derivative can be enlarged with a high yield by only heating without using any acid catalyst.

As substituents, $R_1$ and $R_2$ of the amino group at the 6-position of the formula (I), various kinds of groups other than a hydrogen atom can be employed. Specific examples of $R_1$ and $R_2$ are the univalent groups represented by the formula

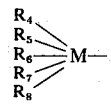

wherein M represents a carbon atom, a nitrogen atom, an oxygen atom, a sulfur atom, a phosphorus atom, or a silicon atom and $R_4$, $R_5$, $R_6$, $R_7$, and $R_8$, which may be the same or different, each represents a hydrogen atom, an alkyl group, an aralkyl group, an aryl group, an alkoxy group, an alkylthio grop, an aralkyloxy group, an aralkylthio group, an aryloxy group, an arylthio group, a heterocyclic ring group, or a halogen atom; optionally, two groups of $R_4$, $R_5$, $R_6$, and $R_7$ may be combined to form an oxo group (=O) or a thioxo group (=S) or they can form any other divalent group and further, optionally, two or three groups of $R_4$, $R_5$, $R_6$, $R_7$, and $R_8$ may not be present.

Specific examples of the divalent groups formed by the combination of groups $R_1$ and $R_2$ are those represented by the groups

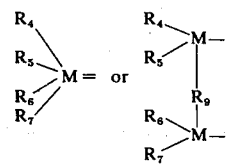

wherein M, $R_1$, $R_2$, $R_3$, $R_4$, $R_5$, $R_6$, and $R_7$ are as defined above and $R_9$ represents an alkylene group or an arylene group and each may have interposed therein an oxygen atom, a sulfur atom, or a nitrogen atom.

Typical examples of the univalent group include a methyl group, an ethyl group, an isobutyl group, a cyclohexyl group, a benzyl group, a phenethyl group, a 2-furylethyl group, a 2-pyridylmethyl group, a trifluoromethyl group, a methoxymethyl group, a phenoxyethyl group, a benzylthioethyl group, a trichloromethyl group, a phenyl group, a naphthyl group, a quinolyl group, a pyridyl group, a piperidyl group, a furyl group, a tolyl group, a p-nitrophenyl group, a phenylacetyl group, a cyclohexylacetyl group, a 2-thienylacetyl group, a 2-furylacetyl group, a cyclopentylcarbonyl group, an α-phenoxyacetyl group, a benzoyl group, a thiobenzoyl group, a nitroso group, a nitro group, an acetylamino group, a benzoylamino group, an N-benzoyl-N-methylamino group, a phenylsulfonyl group, a methylthio group, a naphthylthio group, a dimethoxyphosphinyl group

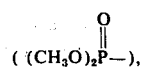

a diphenoxyphosphinyl group

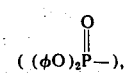

a bis(benzyloxy)phosphinyl group

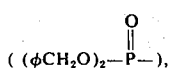

a trimethylsilyl group, a triphenylsilyl group, a dimethylchlorosilyl group, etc. Also, specific examples of the divalent groups are a salycilidene group, a benzylidene group, an oxomethylidene group (O=C=), an α-chlorophenetylidene group, an ethylidene group, an α-imino-phenetyl group, a piperidinomethylidene group, a 1-phenyl-1-dimethylaminomethylidene group, an azo group (—N=N—), a 1-propenylidene group ($CH_3$—CH=C=), a pentamethylene group (—$CH_2CH_2CH_2CH_2CH_2$—), a 1-oxopentamethylene group

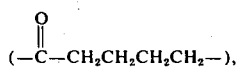

a tetramethylene group (—$CH_2CH_2CH_2CH_2$—), an ethylenedicarbonyl group

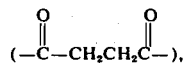

a phthaloyl group

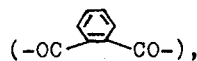

a 3-phenyl-1,1,2-trimethy-4-oxo-2-azatetramethylene group

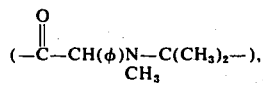

a 1,1-dimethyl-3-phenyl-2-nitroso-4-oxo-2-azatetramethylene group

a 1,4-dioxo-2-butene-1,4-diyl group

an o-phenylenedithiocarbonyl group

etc.

Any groups which do not contribute to the reaction may be employed as group $R_3$ of the compound represented by formula (I) and examples of such groups are a hydrogen atom, a methyl group, an ethyl group, a tert-butyl group, a 2,2,2-trichloroethyl group, a triphenylmethyl group, a bis(p-methoxyphenyl)methyl group, a methoxybenzyl group, a benzhydryl group, a phenacyl group, a p-bromophenacyl group, a 3,5-di-tert-butyl-4-hydroxybenzyl group, a phthalimidomethyl group, a p-toluenesulfonylethyl group, a nitro group, and a halogen-substituted benzyl group.

In accordance with the process of this invention, a compound of formula (I) is usually suspended or dissolved in a solvent which does not contribute to the reaction i.e., an inert solvent, such as pyridine, dioxane, dimethylformamide, xylene, toluene, methyl isobutyl ketone, hexamethapol, etc., and the suspension or the solution thus prepared may be heated to temperatures lower than 180°C., preferably at 80°–120°C. The products of this invention represented by the formula (II) thus obtained are isolated and purified by an ordinary chemical operation such as chromatography, recrystallization, etc., after removing the solvent.

The compounds of this invention represented by formula (II) are antibacterials and also, in particular are useful as starting materials for preparing various cephasporin derivatives useful as antibiotics. For example, when the compound represented by the formula (II′)

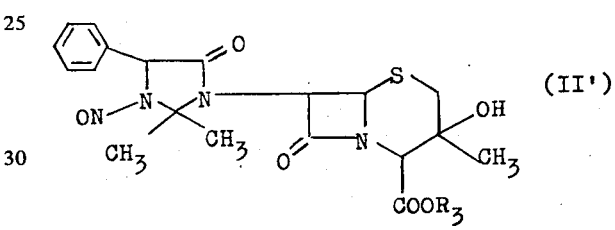

that is the compound of formula (II) in which A is the divalent group represented by the formula

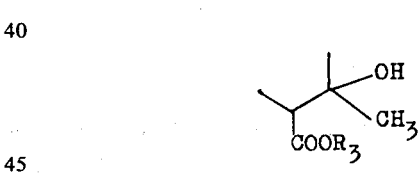

and the divalent group formed by the combination of $R_1$ and $R_2$ is a 1,1-dimethyl-3-phenyl-2-nitroso-4-oxo-2-azatetramethylene group is treated with an acid and then water, a useful antibiotic 7-D-[α-aminophenylacetamido]-3-hydroxy-3-methylcepham-4-carboxylic acid can be obtained. Or, by oxidizing the above compound (II′) to provide the sulfoxide, reacting the product with the halogen compound shown by the formula $SOX_2$ or $POX_3$ (wherein X represents a halogen atom), and then treating the resultant product with an acid and then water, a useful antibiotic cephalexin can be obtained.

The invention will now be illustrated in the following examples.

EXAMPLE 1

In 20 ml. of dioxane was dissolved 500 mg. of methyl 6-(2,2-dimethyl-3-nitroso-4-phenyl-5-oxo-1- imidazolidinyl)penicillinate sulfoxide and the solution was refluxed under heating for 10 hours. The reaction mixture was concentrated under reduced pressure, the residue obtained was dissolved in dichloromethane, and then the solution was washed with a dilute aqueous sodium bicarbonate solution and then water. Thereafter, by drying the solution over anhydrous magnesium sulfate and distilling off the solvent under reduced pressure, a white crystal was precipitated, which was recovered by filtration and washed with ether to provide 440 mg. of methyl 3-hydroxy-3-methyl-7-(2,2-dimethyl-3-nitroso-4-phenyl-5-oxo-1-imidazolidinyl)-cepham-4-carboxylate in a yield of 88 percent.

Melting point 257°C. (decomp.).

Nuclear magnetic resonance spectra (in $D_6$-DMSO):
δ: 1.19 (3H, s), 2.0 (6H, s), AB type 2,43, 2.66, 3.08, 3.31 (2H), 3.71 (3H, s), 4.28 (1H, s), 4.85 (broad s, 1H), 5.2–5.5 AB type (2H), 5.72 (1H, s), 7.3 (5H, s).

| Elemental analysis for $C_{20}H_{24}N_4O_6S$: | | | | |
|---|---|---|---|---|
| | C(%) | H(%) | N(%) | S(%) |
| Calculated: | 53.56 | 5.39 | 12.49 | 7.15 |
| Found: | 53.53 | 5.38 | 12.22 | 7.23 |

Preparation of the Starting Material a. In 30 ml. of ethyl acetate was dissolved 5 g. of 6-(2,2-dimethyl-3-nitroso-4-phenyl-5-oxo-1-imidazolidinyl)penicillanic acid and while stirring the solution at room temperature, an ether solution of 0.05 g. of diazomethane was added to the solution. After the reaction was over, the reaction mixture was washed with a dilute aqueous sodium bicarbonate solution, dried over anhydrous magnesium sulfate, and then the solvent was distilled off. Then, ether was added to the residue and the precipitates formed were recovered by filtration to provide 5.1 g. of methyl 6-(2,2-dimethyl-3-nitroso-4-phenyl-5-oxo-1-imidazolidinyl)penicillanate in a yield of 99 percent.

Melting point 188°C.

Infrared absorption spectra:

$\nu_{max.}^{KBr}$ cm.$^{-1}$: 1790 (β-lactam), 1750, 1730 (C=O).

Nuclear magnetic resonance spectra (in $CDCl_3$):
δ: 1.47 (3H, s), 1.62 (3H, s), 2.10 (6H, s), 3.75 (3H, s), 4.54 (1H, s), 4.95 (1H, d, J=4), 5.45 (1H, s), 5.64 (1H, d, J=4), 7.28 (5H, s).

b. In 20 ml. of chloroform was dissolved 3 g. of methyl 6-(2,2-dimethyl-3-nitroso-4-phenyl-5-oxo-1-imidazolidinyl)penicillanate and while stirring the solution under ice-cooling, a chloroform solution of 960 mg. of perbenzoic acid was added to the solution. After the reaction was over, the reaction mixture was washed with an aqueous sodium bicarbonate solution and then water, dried over anhydrous magnesium sulate, and then the solvent was distilled off under reduced pressure to provide 3.0 g. of methyl 6-(2,2-dimethyl-3-nitroso-4-phenyl-5-oxo-1-imidazolidinyl)penicillanate sulfoxide in a yield of 96 percent.

Infrared absorption spectrum:

$\nu_{max.}^{KBr}$ cm.$^{-1}$: 1045 (S → O).

EXAMPLE 2

In 20 ml. of dioxane was dissolved 500 mg. of 6-(2,2-dimethyl-3-nitroso-4-phenyl-5-oxo-1-imidazolidinyl)-penicillanic acid sulfoxide and the solution prepared was refluxed under heating for 15 hours. Then, by distilling off the solvent from the reaction mixture under reduced pressure, a light brown powder of 3-hydroxy-3-methyl-7-(2,2-dimethyl-3-nitroso-4-phenyl-5-oxo-1-imidazolidinyl)cepham-4-carboxylic acid was obtained.

The powder obtained was suspended in ethyl acetate, an ether solution of diazomethane was added to the suspension, and after the reaction was over, the solvent was distilled off from the reaction mixture. Then, the residue thus formed was dissolved in 40 ml. of dichloromethane and after washing the solution with a dilute aqueous sodium bicarbonate solution and drying it over anhydrous magnesium sulfate, the solvent was distilled off under reduced pressure from the mixture and ether was added to the residue, whereby a white crystal was formed. The amount of the crystal was 460 mg. The infrared absorption spectra and the nuclear magnetic resonance spectra of the product were the same as those of methyl 3-hydroxy-3-methyl-7-(2,2-dimethyl-3-nitroso-4-phenyl-5-oxo-1-imidazolidinyl)cepham-4-carboxylate and when the product was melted together with the abovementioned carboxylate, no melting point reduction was observed.

Preparation of the Starting Material

In 20 ml. of chloroform was dissolved 2 g. of 6-(2,2-dimethyl-3-nitroso-4-phenyl-5-oxo-1-imidazolidinyl)-penicillanic acid and then the chloroform solution of 662 mg. of perbenzoic acid was added to the solution with stirring under cooling. The solvent was distilled off from the reaction mixture under reduced pressure and then ether was added to the residue formed, whereby a white crystal was formed. The crystal was recovered by filtration and washed with ether to provide 1.9 g. of the white crystal of 6-(2,2-dimethyl-3-nitroso-4-phenyl-5-oxo-1-imidazolidinyl)penicillanic acid sulfoxide with a yield of 92 percent.

Melting point 159°C. (decomp.)

EXAMPLE 3

In 20 ml. of dioxane was dissolved 500 mg. of benzhydryl 6-phthalimidopenicillanate sulfoxide and the solvent was refluxed under heating for 18 hours. The solvent was, then, distilled off under reduced pressure from the reaction mixture and then ether was added to the residue formed, whereby a white crystal was formed. The crystal was recovered by filtration to provide 480 mg. of benzhydryl 7-phthalimido-3-hydroxy-3-methylcepham-4-carboxylate with a yield of 96 percent.

Melting point 223°C.

Nuclear magnetic resonance spectra (in $CDCl_3$):
δ: 1.20 (3H, s), AB type, 2.32, 2.55, 3.31, 3.54 (2H), 4.69 (1H, s), 5.06 (1H), AB type, 5.36, 5.43, 5.52, 5.59 (2H), 6.92 (1H, s), 7.35 (10H, s), 7.7–7.95 (4H).

EXAMPLE 4

In 20 ml. of dioxane was dissolved 500 mg. of 6-phthalimidopenicillanic acid sulfoxide and the solution was refluxed under heating for 15 hours. By distilling off the solvent from the reaction mixture under reduced pressure, a light brown powder of 7-phthalimido-3-hydroxy-3-methylcepham-4-carboxylic acid was obtained. The powder was suspended in ethyl acetate, an ether solution of diazomethane was added to the suspension, and after washing the mixture with a dilute aqueous sodium bicarbonate solution and water and drying it over anhydrous magnesium sulfate, the solvent was distilled off under reduced pressure. Then, the residue formed was subjected to a silica gel column chromatography.

The product was recovered from the column using a 9 : 1 by volume benzene-ethyl acetate mixture as an eluant. Then, the solvent was distilled off from the eluate under a reduced pressure and ether was added to the residue formed, whereby 350 mg. of a white crystal of methyl 7-phthalimido-3-hydroxy-3-methylcepham-4-carboxylate was formed.

Melting point 203°C.

Nuclear magnetic resonance spectra (in $CDCl_3$):

δ: 1.36 (3H, s), AB type, 2.42, 2.65, 3.40, 3.63 (2H), 4.58 (1H, s), 5.03 (1H, broad s), AB type, 5.41, 5.48, 5.57, 5.64 (2H), 7.6–8.1 (4H).

| Elemental analysis for $C_{17}H_{16}N_2O_6S$: | | | |
|---|---|---|---|
| | C(%) | H(%) | N(%) |
| Calculated: | 54.25 | 4.28 | 7.44 |
| Found: | 54.19 | 4.41 | 7.35 |

Preparation of the Starting Material

In 150 ml. of chloroform was dissolved 2 g. of 6-phthalimidopenicillanic acid and a chloroform solution of 800 mg. of perbenzoic acid was added to the solution with stirring under ice-cooling. After the reaction was over, the solvent was distilled off from the reaction mixture under reduced pressure and then ether was added to the residue thus formed, whereby a white powder was formed. The powder was recovered by filtration and washed with ether to provide 1.95 g. of 6-phthalimidopenicillanic acid sulfoxide with a yield of 96 percent.

Infrared absorption spectra:

$\nu_{max}^{KBr}$ cm.$^{-1}$: 1015 (S → O), 1720 (COOH).

Nuclear magnetic resonance spectra (in $D_6$-DMSO):

δ: 1.23 (3H, s), 1.66 (3H, s), 4.42 (1H, s), 4.88 (1H, d, J = 4.5), 6.05 (1H, d, J=4.5), 7.90 (4H, broad, s).

EXAMPLE 5

In 33 ml. of dioxane was suspended 835 mg. of methyl 6-salycilideneaminopenicillanate sulfoxide and the suspension was refluxed under heating for 17 hours. The reaction product thus obtained was concentrated and the concentrate was diluted with 30 ml. of ethyl acetate. The solution prepared was washed with water, dried over anhydrous magnesium sulfate, and then the solvent was distilled off under reduced pressure.

The oily matter thus obtained was purified by means of a silica gel column chromatography using benzene as an eluant to provide 633 mg. of a colorless acicular crystal of methyl 3-methyl-7-salycilidene-amino-Δ³-cephem-4-carboxylate in a yield of 82 percent.

Melting point 179°C.

Infrared absorption spectra:

$\nu_{max}^{KBr}$ Cm.$^{-1}$: 3440 (OH), 1760 (lactam), 1730 (ester), 1620 (CH=N).

Nuclear magnetic resonance spectra (in $CDCl_3$):

δ: 2.14 (3H, s), AB type, 3.00, 3.31, 3.41, 3.72 (2H), 3.84 (3H, s), AB type, 5.07, 5.14, 5.27, 5.34 (2H), 6.74–7.5 (4H), 8.59 (1H, s), 12.2 (1H, broad s).

| Elemental analysis for $C_{16}N_{16}N_2O_4S$: | | | | |
|---|---|---|---|---|
| | C(%) | H(%) | N(%) | S(%) |
| Calculated: | 57.82 | 4.85 | 8.43 | 9.65 |
| Found: | 57.50 | 4.71 | 8.00 | 9.71 |

EXAMPLE 6

In 40 ml. of dioxane was dissolved 1 g. of benzhydryl 6-(2,2-dimethyl-3-nitroso-4-phenyl-5-oxo-1-(imidazolydinyl)penicillanate sulfoxide and the solution was refluxed under heating for 1 hour and 15 minutes. The solvent was distilled off under reduced pressure from the reaction mixture thus obtained, the residue formed was subjected to a silica gel column chromatography, and the product was eluted from the column using a 6 : 1 (by volume) benzene-ethyl acetate mixture as an eluant. The solvent was distilled off under reduced pressure from the eluate to provide 948 mg. of a white crystal of benzhydryl 3-hydroxy-3-methyl-7-(2,2-dimethyl-3-nitroso-4-phenyl-5-oxo-1-imidazolydinyl)cepham-4-carboxylate.

Nuclear magnetic resonance spectra (in $CDCl_3$):

δ: 1.09 (3H, s), 1.96 (6H, s), AB type, 2.15, 2.39, 3.19, 3.43 (2H), 4.57 (1H, s), 4.58 (1H, d, J = 4.0), 4.93 (1H, broad s), 5.35 (1H, d, J = 4.0), 5.49 (1H, s), 6.89 (1H, s), 7.3 (15H).

What is claimed is:

1. A process for the preparation of a cephalosporanic acid derivative represented by the formula

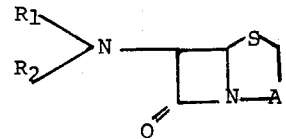

wherein $R_1$ and $R_2$, which may be the same or different, each represents a univalent group, selected from the group consisting of lower alkyl, cyclohexyl, benzyl, phenethyl, 2-furylethyl, 2-pyridylmethyl, trifluoromethyl, methoxymethyl, phenoxyethyl, benzylthioethyl, trichloromethyl, phenyl, naphthyl, quinolyl, pyridyl, piperidyl, furyl, tolyl, p-nitrophenyl, phenylacetyl, cyclohexylacetyl, 2-thienylacetyl, 2-furylacetyl, cyclopentylcarbonyl, α-phenoxyacetyl, benzoyl, thiobenzoyl, said $R_1$ and $R_2$ may be combined to form a divalent group selected from the group consisting of salicylidene, benzylidene, oxomethylidene, α-chlorophenethylidene, ethylidene, α-imino-phenethyl, piperidinomethyl-idene, 1-phenyl-1-dimethylamino methylidene, 1-propenylidene,pentamethylene, 1-oxopentamethylene, tetramethylene, ethylene-dicarbonyl, phthaloyl, 3-phenyl-1,1,2-trimethyl-4-oxo-2-azatetramethylene, 1,1-dimethyl-3-phenyl-2-nitroso-4-oxo-2-azatetramethylene, 1,4-dioxo-2-butene-1,4-diyl, and o-phenylenedithiocarbonyl, and A represents a divalent group represented by the formulae

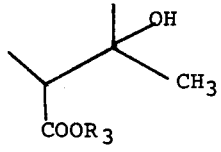

or

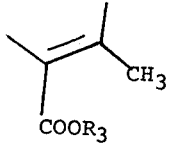

wherein $R_3$ represents a hydrogen atom, a methyl group, an ethyl group, a tert-butyl group, a 2,2,2-trichloroethyl group, a triphenylmethyl group, a bis(p-methoxyphenyl)methyl group, a methoxybenzyl group, a benzhydryl group, a 3,5-di-tert-butyl-4-hydroxybenzyl group, a phthalimidomethyl group, a p-toluenesulfonylethyl group, or a halogen-substituted benzyl group which consists essentially of heating the penicillin sulfoxide derivative represented by the formula

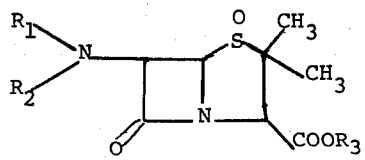

wherein $R_1$ and $R_2$ are as defined above at a temperature up to about 180°C in an inert organic solvent.

2. The process of claim 1 wherein

is 2,2-dimethyl-3-nitroso-4-phenyl-5-oxo-1-imidazolidinyl and $R_3$ is methyl.

3. The process of claim 1 wherein

is 2,2-dimethyl-3-nitroso-4-phenyl-5-oxo-1-imidazolidinyl and $R_3$ is hydrogen.

4. The process of claim 1 wherein

is phthalimido and $R_3$ is benzhydryl.

5. The process of claim 1 wherein

is phthalimido and $R_3$ is hydrogen.

6. The process of claim 1 wherein

is salicylideneamino and $R_3$ is methyl.

7. The process of claim 1 wherein

is 2,2-dimethyl-3-nitroso-4-phenyl-5-oxo-1-imidazolidinyl and $R_3$ is benzhydryl.

* * * * *